(12) United States Patent
Becker (10) Patent No.: US 11,202,366 B2
(45) Date of Patent: Dec. 14, 2021

(54) OBJECT HAVING AN ELECTRONIC UNIT AND CONDUCTOR STRUCTURES ON A CARRIER STRUCTURE

(71) Applicant: Schreiner Group GmbH & Co. KG, Oberschleissheim (DE)

(72) Inventor: Johannes Becker, Ilmmuenster (DE)

(73) Assignee: Schreiner Group GmbH & Co. KG, Oberschleissheim (DE)

(*) Notice: Subject to any disclaimer, the term of this patent is extended or adjusted under 35 U.S.C. 154(b) by 753 days.

(21) Appl. No.: 15/752,669

(22) PCT Filed: Aug. 18, 2016

(86) PCT No.: PCT/EP2016/069600
§ 371 (c)(1),
(2) Date: Feb. 14, 2018

(87) PCT Pub. No.: WO2017/032684
PCT Pub. Date: Mar. 2, 2017

(65) Prior Publication Data
US 2018/0249573 A1    Aug. 30, 2018

(30) Foreign Application Priority Data
Aug. 21, 2015 (DE) .................. 10 2015 113 928.6

(51) Int. Cl.
*H05K 1/02* (2006.01)
*H05K 1/14* (2006.01)
(Continued)

(52) U.S. Cl.
CPC ............ *H05K 1/028* (2013.01); *A61F 13/42* (2013.01); *A61J 1/035* (2013.01); *B65D 75/367* (2013.01);
(Continued)

(58) Field of Classification Search
CPC ..... A61F 13/42; A61F 2013/424; A61J 1/035; A61J 2200/70; B65D 75/367;
(Continued)

(56) References Cited

U.S. PATENT DOCUMENTS 5,466,892 A   11/1995   Howard et al.
5,818,112 A   10/1998   Weber et al.
(Continued)

FOREIGN PATENT DOCUMENTS

CN    1795555 A    6/2006
CN    101151946 A   3/2008
(Continued)

OTHER PUBLICATIONS

International Search Report of PCT/EP2016/069600, dated Jan. 2, 2017.
(Continued)

*Primary Examiner* — Son T Le
*Assistant Examiner* — Adam S Clarke
(74) *Attorney, Agent, or Firm* — Collard & Roe, P.C.

(57) ABSTRACT

An object has a first conductor structure, an electronic unit, a second conductor structure galvanically isolated from the first conductor structure and/or from the electronic unit but coupleable electrically thereto, and a carrier structure with a first pliable carrier layer having a first carrier layer region and with a second carrier layer region. The carrier structure is a layer stack in a base surface region including at least part of the carrier structure base surface and includes at least the first and second carrier layer regions. At least part of the conductor structures is in the base surface region. The first conductor structure and/or the electronic unit is joined with the first carrier layer region. The second conductor structure is joined with the second carrier layer region and coupleable electrically to the first conductor structure and/or the elec- (Continued)

tronic unit by a layer stack surface region outside the electronic unit.

27 Claims, 6 Drawing Sheets

(51) Int. Cl.
  *A61F 13/42* (2006.01)
  *A61J 1/03* (2006.01)
  *B65D 75/36* (2006.01)
  *G01N 27/22* (2006.01)
  *H05K 1/18* (2006.01)
  *H05K 1/16* (2006.01)

(52) U.S. Cl.
  CPC ......... *G01N 27/223* (2013.01); *H05K 1/0239* (2013.01); *H05K 1/147* (2013.01); *H05K 1/18* (2013.01); *A61F 2013/424* (2013.01); *A61J 2200/70* (2013.01); *H05K 1/162* (2013.01); *H05K 1/165* (2013.01); *H05K 2201/049* (2013.01); *H05K 2201/055* (2013.01); *H05K 2201/056* (2013.01); *H05K 2201/09663* (2013.01); *H05K 2201/09672* (2013.01); *H05K 2201/1003* (2013.01); *H05K 2201/10015* (2013.01); *H05K 2201/10098* (2013.01); *H05K 2201/10151* (2013.01); *H05K 2201/10681* (2013.01)

(58) Field of Classification Search
  CPC .... G01N 27/223; H05K 1/0239; H05K 1/028; H05K 1/147; H05K 1/162; H05K 1/165; H05K 1/18; H05K 2201/049; H05K 2201/055; H05K 2201/056; H05K 2201/09663; H05K 2201/09672; H05K 2201/10015; H05K 2201/1003; H05K 2201/10098; H05K 2201/10151; H05K 2201/10681
  See application file for complete search history.

(56) References Cited

U.S. PATENT DOCUMENTS

| | | |
|---|---|---|
| 6,310,536 B1 | 10/2001 | Hellriegel |
| 7,057,116 B2 | 6/2006 | Reid et al. |
| 8,859,909 B2 | 10/2014 | Dimmock |
| 2004/0227230 A1 | 11/2004 | Chou |
| 2010/0085258 A1 | 4/2010 | Teshima et al. |
| 2011/0157536 A1* | 6/2011 | Inui .................. H05K 1/0281 349/151 |
| 2013/0015246 A1 | 1/2013 | Galfe et al. |
| 2013/0230755 A1 | 9/2013 | Dimmock |
| 2014/0307396 A1* | 10/2014 | Lee .................. H05K 1/028 361/749 |
| 2015/0249059 A1* | 9/2015 | Maijala .............. H01L 23/642 257/664 |
| 2016/0014884 A1 | 1/2016 | Diegel et al. |
| 2018/0125761 A1* | 5/2018 | Conlon ............... B65B 9/045 |
| 2019/0103181 A1* | 4/2019 | Lesau ................ A61J 1/035 |

FOREIGN PATENT DOCUMENTS

| | | |
|---|---|---|
| CN | 104704928 A | 6/2015 |
| DE | 44 26 908 A1 | 2/1996 |
| DE | 10 2009 018 285 A1 | 11/2010 |
| DE | 10 2010 005 714 A1 | 7/2011 |
| DE | 10 2009 005 100 B4 | 6/2012 |
| DE | 20 2014 103 821 U1 | 9/2014 |
| DE | 10 2014 118 353 A1 | 6/2016 |
| EP | 0 714 130 B1 | 1/2002 |
| EP | 1 416 581 A1 | 5/2004 |
| EP | 1 893 995 B1 | 10/2014 |
| WO | 2016/091964 A1 | 6/2016 |

OTHER PUBLICATIONS

Wah, Y. C. et al: "Foldable Y-Shape Flex", Motorola Technical Developments, Motorola Inc., vol. 32, Sep. 1997, pp. 21-22.

Soldner, K. et al: "Post Assembly Multi-Layer Interconnects for Flexible Circuits" Motorola Technical Developments, Motorola Inc., vol. 10, Mar. 1990, pp. 19-20.

* cited by examiner

OBJECT HAVING AN ELECTRONIC UNIT AND CONDUCTOR STRUCTURES ON A CARRIER STRUCTURE

CROSS REFERENCE TO RELATED APPLICATIONS

This application is the National Stage of PCT/EP2016/069600 filed on Aug. 18, 2016, which claims priority under 35 U.S.C. § 119 of German Application No. 10 2015 113 928.6 filed on Aug. 21, 2015, the disclosure of which is incorporated by reference. The international application under PCT article 21 (2) was not published in English.

The Application relates to an object with an electronic unit and with conductor structures on a carrier structure; in particular, an object that has, on a carrier structure, at least one first conductor structure, at least one electronic unit and at least one second conductor structure, wherein the second conductor structure is galvanically isolated from the first conductor structure and/or from the electronic unit, but can be coupled electrically thereto.

In the most diverse fields of technology, objects are in use that have one or more electronic units mounted on a carrier structure. Such electronic units may be, for example, active or passive structural elements, such as resistors, capacitors, inductors, other electrical or electronic piece parts or even more complex electronic units, such as chips with electronic or microelectronic circuits. An electronic unit may also be a sensor unit, which, for example, comprises a sensor element for measurement of any appropriate physical variable or of a parameter and/or its parameter value, or in any case is joined or can be joined to such a sensor element. This listing of exemplary conceivable electronic units is not exhaustive and could be expanded at will. Furthermore, an electronic unit may also comprise a multiplicity of electrical and/or electronic structural elements, chips and/or other piece parts; for example, several electronic elements that are structurally isolated but respectively are joined individually to the carrier structure may together form an electronic unit; corresponding to the overall function of this group of piece parts.

For example, evaluation electronics for moisture measurements or moisture sensors, evaluation electronics for detection and/or for time-stamping of interruptions in conductor tracks, of short circuits between conductor tracks or of temporary changes of the capacitance of capacitors or of the inductance of inductors may be mentioned here; for instance as a function of external environmental influences or human interactions. Furthermore, chips and/or transponders for near-field communication are conceivable as electronic units, for example RFID chips or chips for communication via Bluetooth or WLAN.

Such objects have a carrier structure on which or within which conductor structures, especially conductor tracks, are also disposed.

Most objects possess rigid carrier structures, for example printed circuit boards (PCBs) or other carrier plates, which by design are rigid and, for example, can be screwed together with a housing. However, objects with flexible, i.e. pliable carrier structures also exist, namely objects in which the electronic unit and/or the conductor structures are applied on a foil.

As an example of these, moisture sensors for anti-incontinence diapers may be mentioned in which moisture or wetness can be detected by altered capacitance or inductance values or by electrical short circuits, and in which, however, a rigid carrier structure would be unsuitable in view of the body's shape.

Furthermore, blister packs for tablets, medicine capsules or other dosage units exist that are bent and locally damaged by the patient or by the medical personnel during opening, which can be detected and evaluated as an interruption of the electrical conductor associated with the respective tablet or capsule and/or the surrounding cavity. Any interruption of a conductor track is then interpreted and time-stamped as removal or ingestion by the patient.

Furthermore, electronic seals, for example, exist that generate and maintain a closed electrical circuit, in which case any destruction caused by an unauthorized intervention or temporary interruption of the closed electrical circuit or any change of capacitance or inductance values can be electronically sensed and verified as a seal rupture.

Such and other objects can in principle also be produced with use of a foil or any other flexible, i.e. pliable carrier structure, but the foil-based manufacture of such and other objects is conventionally poorly efficient.

If, for example, electronic units or sub-components thereof are soldered onto a plastic foil, foils of temperature-resistant material, for example with working temperatures above 250° C., are needed, although they increase the manufacturing expense and the material costs. Alternatively, low-melting solders may be used, but they are likewise considerably more expensive. The surface mounting or soldering of electronic components onto flexible plastic foils is poorly efficient in particular if only relatively few soldered joints have to be made on expansive, i.e. large-area foils, or if the solder junctions have to be produced only at one or at a few surface regions, which are relatively small in comparison with the total foil surface.

Instead of soldered joints, it is also possible to apply a conductive adhesive in order to join electronic units conductively with the foil. However, conductive adhesives cure only slowly, which in turn slows the material throughput of the manufacturing process; therefore a certain time is also needed for the manufacture of conductive adhesive joints. The cooling or curing time necessary for the soldered or conductive adhesive joints is independent of the foil size in other surface regions, apart from the soldered or conductive adhesive joints. Precisely for large foils with few electrical contact junctions, the fabrication, especially the assembly and mounting of electronic components and units, quickly becomes uneconomical.

In addition, existing systems and processes for assembly or contacting of electronic components have limited throughput. For predetermined number of electronic components per unit of the object to be manufactured, the speed, for example, of placement of a component on the carrier structure is limited by the manufacturing apparatus; furthermore, the volume or the base surface in assembly and contacting systems is limited and, depending on size of the product, is rapidly exhausted before the material for the next batch of units of the object to be manufactured is supplied.

It is the task of the present Application to provide an object that has an electronic unit and conductor structures on a carrier structure but that can nevertheless be manufactured for lower total costs and lower manufacturing expense and therefore is more cost-effective. It is further the task of the present Application to provide a suitable manufacturing process.

This task is accomplished by the object of claims 1, 25 and 27.

Some exemplary embodiments are described in the following with reference to the figures, wherein.

According to the invention, it is proposed, instead of a single foil, which is conventionally used as a carrier structure for the electronic unit and for conductor tracks, to configure the carrier structure at least regionally, especially in a part of its base surface, as a layer stack, i.e. as a layer composite, which comprises at least two foils or foil portions or two other carrier layer regions, which are stacked one on the other or one above the other; if necessary with an adhesive layer or other intermediate layer disposed between them. In most of the embodiments yet to be described in detail in the following, this indeed requires the addition and processing of a further, additional foil or carrier layer, which is why such a solution seems a priori far from promising to the person skilled in the art as regards lowering the costs and the manufacturing expense.

However, the additional foil or carrier layer makes it possible to subdivide the total foil surface or base surface of the carrier structure that is necessary on the whole into base surfaces of two separate carrier layers and one overlap surface, in which the two carrier layers are stacked one above the other, in such a way that, from the viewpoint of throughput optimization during processing and assembly of the respective single foils, an ultimate gain in production time and/or material throughput can nevertheless be achieved. For example, starting from a total base surface that is conventionally filled by a single foil, it is possible to reduce the base surface of that foil which is to be assembled with the electronic unit so much that this foil extends in lateral direction only over the immediate surroundings of the electronic unit, whereas surface regions further removed are filled only by the other, second foil or carrier layer. The foil to be assembled with the electronic unit does not need to project beyond the other foil at all, but instead is able to occupy only part of it, approximately a base surface region in which it is stacked on it, for instance is adhered to it in surface-to-surface manner.

The second conductor structure, which may comprise, for example, a second conductor track connected to a second contact terminal of the electronic unit, a capacitor plate, an inductor, an antenna and/or an electrode, is disposed on the other, second foil. The conductor structures on the two carrier layers or foils may be conductor structures that are applied by printing technology, i.e. without assistance of soldered joints or conductive adhesive joints, or conductor structures manufactured in other ways. Although they are disposed on different foils or carrier layers, they do not have to be joined conductively with one another, but instead may remain galvanically isolated from one another, provided at least one alternating-current circuit can be generated between them. Therefore the foil equipped with the first conductor structure and the electronic unit does not have to be soldered or brought by means of conductive adhesive into conductive contact with the second foil on which the second conductor structure is disposed. In terms of production engineering, it is sufficient to join the two foils or carrier layers to one another by an adhesive or lamination process after their production and assembly, whereby the ready-to-use object is obtained.

The soldering or otherwise contacting of the electronic unit, especially with the smaller of the two foils or carrier layers, may therefore be performed with increased throughput rate and thus particularly efficiently. In addition, the other, larger foil, which is exposed beforehand only to printing processes, can also be manufactured in larger output rates per time unit.

The first and the second conductor structure may be galvanically isolated from one another but coupled capacitively or inductively to one another, for example by capacitor plates or inductors or induction coils, associated with one another, disposed on both foils. By application or excitation of an alternating voltage or an alternating current, a capacitive or inductive coupling is created through both foils and any intermediate layer or adhesive layer that may be disposed in between, without impairing the functional performance of the electronic unit by the regionally doubly laid foil.

Figure 1:
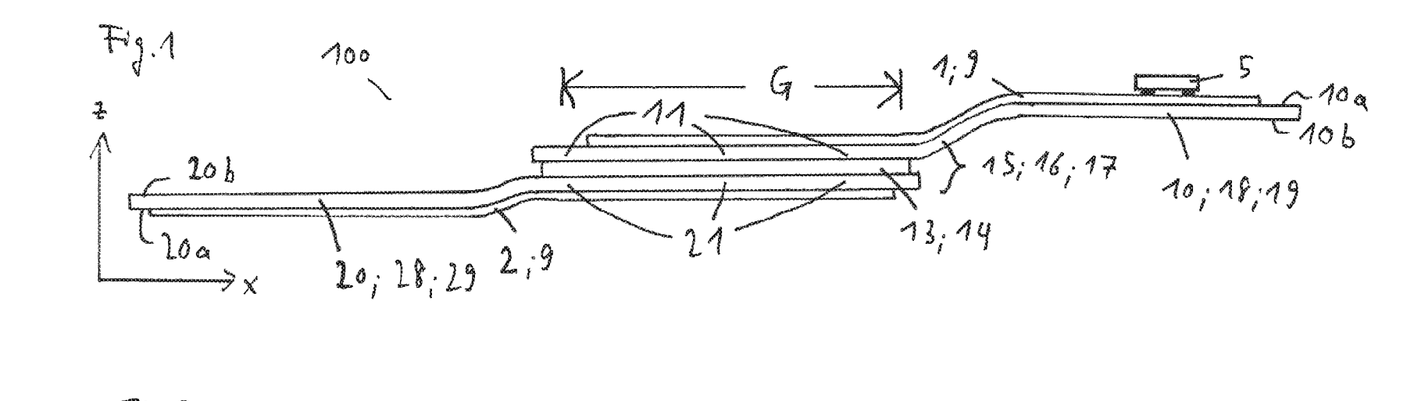
FIG. 1 shows a schematic cross-sectional view of a first exemplary embodiment of an object according to the invention.
Figure 2:
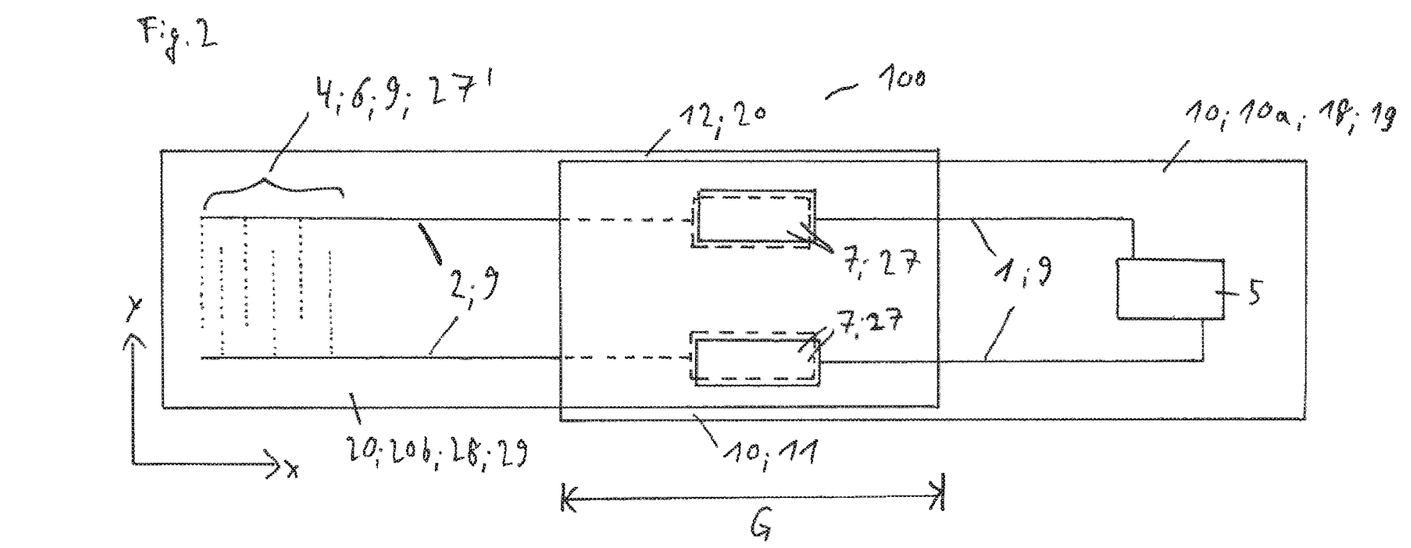
FIG. 2 shows a schematic overhead view of the object according to FIG. 1.

The coupling of the two conductor structures to one another or of the second conductor structure to the first conductor structure and/or to the electronic unit takes place according to this Application not by the electronic unit itself but instead by the layer stack, which comprises the two carrier layers or carrier layer regions (e.g. two foils or foil portions) with the first and the second conductor structure. The electronic unit is situated outside, i.e. relative to the base surface, laterally outside that part of the base surface of the layer stack, in which base surface part the electrical coupling between the two conductor structures or the coupling of the second conductor structure to the first conductor structure and/or with the electronic unit takes place. In particular, the electronic unit may be disposed outside the base surface of the layer stack. Thus the layer stack in particular may be disposed outside the electronic unit, i.e. the base surface of the layer stack and the base surface of the electronic unit do not overlap one another (FIGS. 1 and 2). Alternatively (FIGS. 3 to 12), the base surface of the layer stack may comprise the base surface of the electronic unit, but project laterally beyond this. In all of these cases, the electrical coupling between the first and the second conductor structure takes place in a partial region of the layer stack or its base surface that is not filled with the electronic unit (or in one not covered with the electronic unit).

In particular, by means of the layer stack, the second conductor structure may be joined by capacitive or inductive coupling to the first conductor structure. For example, whereas the one partial piece or end piece of the first conductor track is coupled in the region of the layer stack to a corresponding partial piece or end piece of the second conductor track, an opposite partial piece or end piece of the first conductor track is joined to the electronic unit. In this way, the second conductor track, for example, may become or be coupled—as is also illustrated in the figures discussed in the following—to the electronic unit via the layer stack and the first conductor track, even though the second conductor track is galvanically isolated from it. Furthermore, as illustrated, several second conductor tracks in particular may also become coupled or be coupled to the electronic unit via corresponding surface regions of the layer stack and via corresponding first conductor tracks.

Specifically, FIG. 1 shows a first exemplary embodiment of an object 100 in schematic cross-sectional view. Instead of only a single foil or carrier layer, as is conventional, both a first carrier layer 10 and also a second carrier layer 20 are provided according to the invention; the two overlap at least in a base surface region G, which corresponds on the whole to a sub-region of the base surface of the carrier structure 15. The carrier structure 15 therefore comprises both carrier layers 10, 20; these may optionally be present as foils 19 and 29, especially plastic foils, or alternatively as other kinds of material films 18 and 28, for instance as plastic films (possibly polyurethane films) or as lacquer films or lacquer layers. Material films 18, 28, i.e. film-like thin layers of suitable material, can be printed on any appropriate substrate surfaces, stripped from these once again and then handled individually, similarly to plastic foils. The at least one second conductor structure 2 may be applied by printing technology, for example, on the second carrier layer 2, i.e. on the second foil 29 or the second material film 28, for example as silver conductive paste or other electrically conductive printed coating. In the same way, the at least one first conductor structure 1 may be applied on the first carrier layer. Apart from conductor tracks 9, both conductor structures 1, 2 may further comprise capacitor plates 7, inductors and/or induction coils and/or sensors, especially printed, laminated or pasted sensors.

In addition, the at least one electronic unit 5 is attached to the first carrier layer 10 by means of solder material or conductive adhesive material. Although the same process steps take place here as in application of the electronic unit on a single foil by soldering or conductive adhesive technology, the base surface of the first foil may be chosen to be so small in comparison with the base surface of the second foil (see the following figures) that a much larger number of first foils can be produced simultaneously, for example assembled in one mounting unit together with electronic units 5, whereas a large number of second foils of relatively large base surface can be produced with increased throughput rate in a process step independent of this and in separate systems, including the printing of the second conductor structures. The manufacture of the larger second foils is therefore not hindered or delayed by the assembly of the smaller first foils.

It is therefore not necessary to subject the second carrier layer 20; 28; 29 to a soldering process or to the application of conductive adhesive material, as is conventionally necessary in the context of the assembly of a single foil with electronic components or units. To the contrary, it is sufficient to dimension the first foil 10 to be assembled such that it corresponds to the base surface and/or position of the electronic unit 5 and to configure the other, predominant part of the carrier structure 15 on the whole by means of the other second carrier layer 20, foil 29 or material track 28 alone.

Only in a smaller base surface region G, in which the two carrier layers 10, 20 overlap one another, do both carrier layers 10, 20 have to be provided and stacked one above the other and if necessary fastened to one another or to an adhesive or other intermediate layer.

Optionally, the carrier layer 10 assembled with the electronic unit 5 may additionally also extend regionally beyond the base surface of the larger carrier layer 20, as is illustrated in FIG. 1. This is not necessary, however; it is sufficient to attach, in only one sub-region of the base surface of the carrier layer 20, a much smaller carrier layer 10 which, however, is already assembled with the electronic unit 5. In this case, the need for longer conductor structures 1 or conductor tracks 9 on this carrier layer 10 may also be obviated if, for example, the electronic unit 5 is already positioned in the region of the foil composite or layer composite formed by the layer stack 16.

In this way an object with a carrier structure 15 is provided which is formed as a layer stack 16 in a base surface region G, which on the whole comprises at least one partial surface of the base surface of the carrier structure 15, wherein the layer stack 16 in the base surface region 15 comprises a first carrier layer region 11 and a second carrier layer region 12. The first carrier layer region 11 is a sub-region of the first carrier layer 10, or of the first foil 19 or of the first material film 18, especially a partial surface region. According to FIG. 1, the second carrier layer region 12 is a surface region, overlapping the foregoing, of another, second carrier layer 20, or of a second foil 29 or of a second material film 28. Both partial layer regions 11, 12 are stacked one above the other, i.e. integrated into a layer stack 16 or layer composite 17. An intermediate layer 14, for instance in the form of an adhesive layer 13 or lamination layer, is preferably disposed between them, although this is optional and may be omitted, for example if both carrier layer regions 11, 12 are pressed against one another and/or held against one another in the region of base surface G by a housing of the object. Furthermore, at least one part of the second conductor structure 2 and preferably also one part of the first conductor structure 1 is disposed in the region of the layer stack 16 or of the base surface G (this applies preferably for all figures and other embodiments of the Application), even though these conductor structures or parts of them do not have to fill the entire base surface G of the layer stack.

The electronic unit 5 in FIG. 1 and the subsequent figures may be any appropriate electronic unit that was mentioned in the introductory passages of this Application. Even the first conductor structure 1 and/or the second conductor structure 2 may be formed as described in the introductory comments; especially as a conductor track 9, antenna 3, inductor, induction coil 8 and/or as a capacitor plate 7. Alternatively, the conductor structures 1, 2 of one or some of them may be constructed as a sensor element of a control element, for example of a control button. With regard to the number of provided conductor structures, it is possible, for example, to provide respectively one first and one second conductor structure 1; 2 or respectively two first and two second conductor structures 1; 2 (for instance, as in FIG. 1).

Depending on function of the electronic unit 5 and on two-dimensional or three-dimensional structure of the object 100, the most diverse objects may be manufactured more cost-effectively and more efficiently than conventionally. Thus the object 100 shown only schematically in FIG. 1 may be, for example, a moisture sensor 101, for instance for incontinence diapers, but alternatively also a blister pack, an electronic seal, a sensor device for any appropriate parameter, as already explained in the introduction, or a transponder for RFID or other NFC applications, to mention only some examples.

The profile of the first and second carrier layer regions 11, 12 or carrier layers 10, 20, which in FIG. 1 is curved in places, as is illustrated at least in regions laterally close to the base surface G of the overlap region, indicates that these carrier layer regions or carrier layers may, according to a first embodiment, be flexible, i.e. pliable, and therefore may possess a bent or bendable shape. For example, both carrier layer regions or carrier layers may be pliable.

Secondly, it is alternatively conceivable that only one of the two carrier layers is pliable, for example that on which the electronic unit and the first conductor structure are disposed, or alternatively that carrier layer on which the second conductor structure is disposed.

Furthermore, it is conceivable that the carrier structure or both of its carrier layers or one of the two carrier layers is pliable or deformable only locally, i.e. only regionally; for instance in a surface region in which, by design, it is intended that a fold or crease line, a local bend, especially bending back of the respective layer, or other deformation, can be formed. Such an at least local deformation can be utilized to guide one of the two conductor structures onto the electronic unit and/or onto the other conductor structure and thus to permit a closed alternating current circuit. For example, the first carrier layer region and/or the second carrier layer region or a partial surface portion thereof may be pliable, for instance by bending back, turning back or in some other way guiding at least one of the carrier layer regions onto the other carrier layer region or a partial surface portion thereof.

In such embodiments in which the entire carrier structure is not pliable, those carrier layers or carrier layer regions that are not pliable or in any case are not predestined for easy bending may be rigid, possess a larger layer thickness or possess a smaller elasticity and/or pliability than those carrier layers or carrier layer regions that are designed at least locally for bending or other manner of deformation.

Furthermore, it is conceivable that only the conductor structures or at least one of them is pliable, either over the full surface or at least locally. For example, it is conceivable that a conductor structure that indeed is fastened to one of the two carrier layers, albeit not over the full surface, i.e. rests on the carrier layer not with its entire surface or underside, but only over part of its surface, is raised locally from the carrier layer, in order to guide it onto the respective other conductor structure and/or onto the electronic unit.

Depending on which of the above embodiments is constructed, the object, its carrier structure, its carrier layers or carrier layer regions and/or its conductor structures may be made to conform to other bodies, provided they are completely or at least locally pliable, for example in order to reach locations to which the electronic unit 5 itself can be guided not at all or not sufficiently closely.

The carrier layers 10, 20 may in particular be foils 19, 29 or material films 18, 28 of suitable plastics or other, especially pliable, materials. Optionally, the layer stack 16 or layer composite 17 formed in the overlap region of both carrier layers 10, 20 is likewise pliable.

FIG. 2 shows a schematic overhead view of the object from FIG. 1. One part of the second carrier layer 20 is disposed underneath one part of the first carrier layer 10. In the region of overlap with the base surface G, the first and second conductor structures 1, 2 respectively comprise conductor track portions of conductor tracks 9 as well as capacitor plates 7 associated with one another. The capacitors 27 formed thereby permit a coupling between the conductor structures 1, 2 of both carrier layers 10, 20 by an alternating current circuit; for instance by application to or induction of an alternating voltage in the (alternating current) circuit formed by the first and second conductor structures. The first conductor structures 1 are connected with one end to the electronic unit 5 and with the other end to a respective capacitor plate 7. Associated capacitor plates 7 of the second conductor structures 2 are situated overlapping this, i.e. under it and if necessary isolated by an intermediate layer 14 or adhesive layer 13 as well as the layer thicknesses of one or both carrier layers 10, 20. The second conductor structures 20 further comprise other conductor tracks 9, which either may extend linearly with open end (left in FIG. 2) or, alternatively, as shown by dotted lines in FIG. 2, may comprise an interdigital structure. However, even without such an interdigital structure, the pair of second conductor structures 2 forms a capacitor, which is usable, for example, for humidity measurement in the ambient air. Length and/or mutual spacing of the two second conductor structures 2 from one another on the second carrier layer 20 are chosen appropriately. The second conductor structures 2; 9 or in any case end pieces or partial pieces thereof may further comprise a sensor element 4 for any appropriate parameter or a contact sensor, for instance a capacitive or inductive contact sensor for a control panel or a control element, for instance for a keyboard. It may be possible for the alternating current circuit for operation of the object 100 to be generated by the electronic unit 5 itself or by externally induced wireless transmission, for instance by RFID or otherwise.

Figure 3:
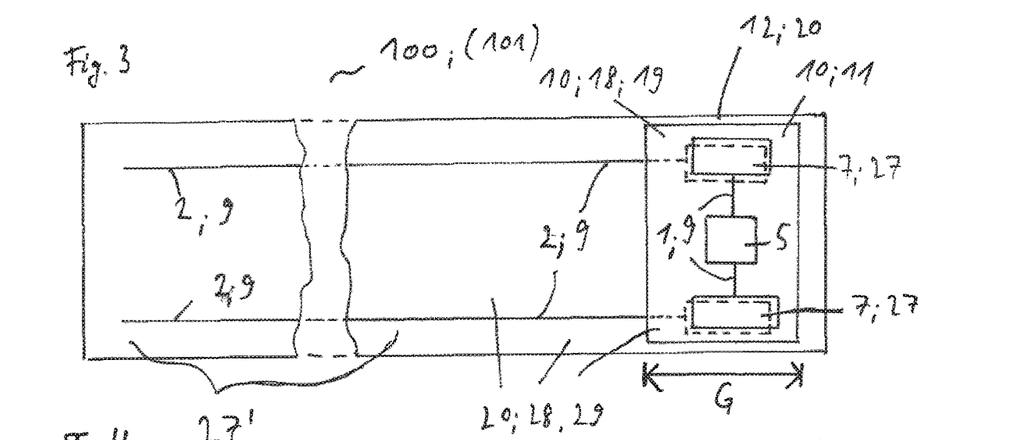
FIG. 3 shows an overhead view of a second embodiment of the object.

FIG. 3 shows an overhead view of another embodiment of an object. In contrast to FIG. 2, the first carrier layer 10 or foil 19 or material track 18 does not reach beyond the second 20; 28; 29 in lateral direction, but instead extends completely within a partial surface region thereof, for example at an end rim (right in FIG. 3). Otherwise, as regards FIG. 3 as well as all subsequent figures, reference is made once again to the explanations for FIGS. 1 and 2 as well as to introductory comments of the description.

In FIG. 3, the capacitor 27' is constructed in the form of two parallel, unbranched conductor tracks 2; 9. If the object 100 comprises a housing (not illustrated), this needs to envelop only the overlap region of both carrier layers 10, 20; this likewise applies for all other figures and other embodiments of the Application. In FIG. 3, a housing attached at the rim end (right in FIG. 3) is sufficient, while the largest surface fraction of the first carrier layer 10 or foil may project out of the housing.

Figure 4:
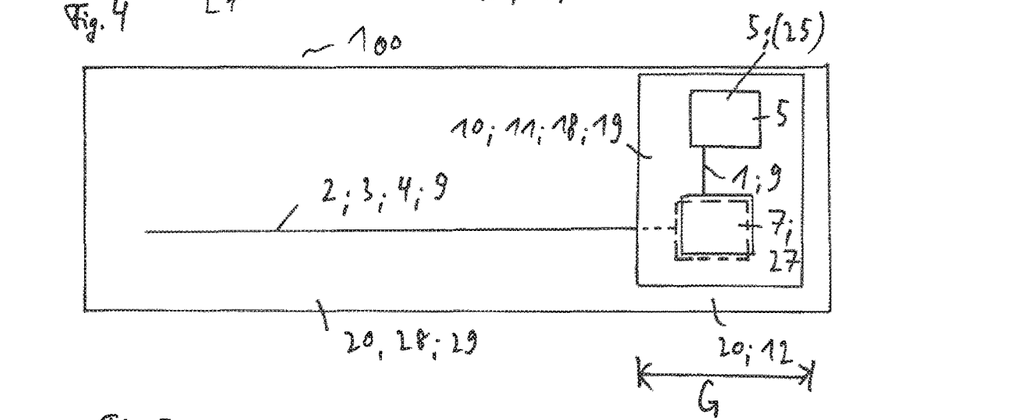
FIG. 4 shows an alternative embodiment of an object with a single first and single second conductor structure.

FIG. 4 shows an alternative embodiment of an object 100, which has only one single, continuous first conductor structure 1 and only one single, continuous conductor structure 2 on the respective foil. The coupling between the two foils or their conductor structures is again established by the capacitor 27. The second conductor structure comprises, other than the capacitor plates 7, mainly an unbranched conductor track 9, the length of which substantially determines the length of the second foil 20 in the direction of a first lateral direction x (compare with FIGS. 1 and 2). In the embodiment of FIG. 4, the second conductor structure 2; 9 forms an antenna 3 or another sensor element 4; the closing of the alternating current circuit is established via frame or ground and thus again wirelessly. The electronic unit 5 may comprise, for example, an RFID chip 25, any other NFC chip and/or any other kind of transponder.

Figure 5:
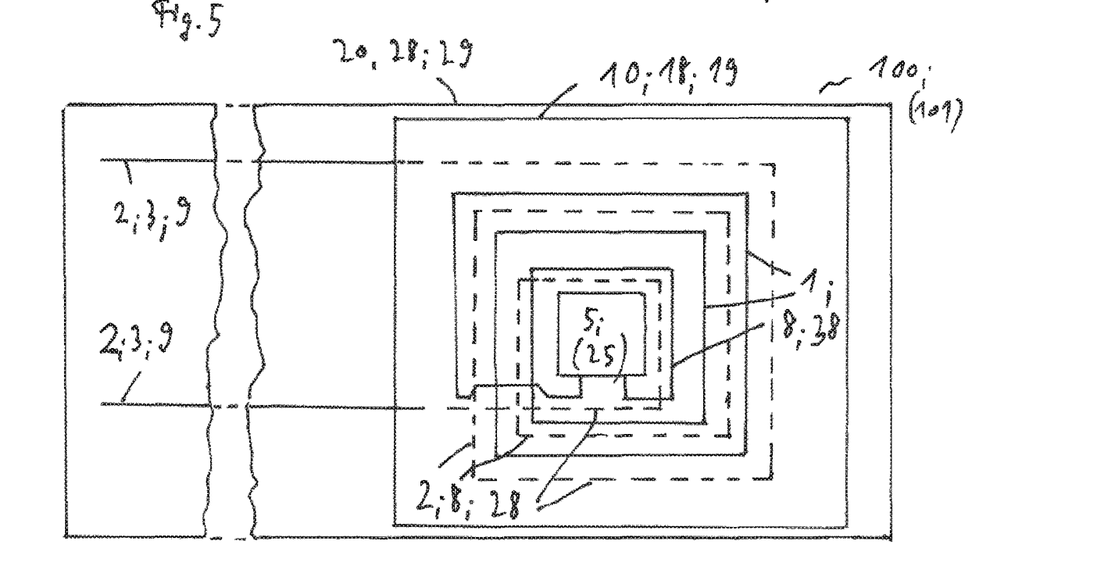
FIG. 5 shows an exemplary embodiment of an object with inductive instead of capacitive coupling.

FIG. 5 shows a further embodiment with an inductive instead of capacitive coupling between the conductor structures of the two foils. The first conductor structure 1 connected to two terminals of the electronic unit 5 forms an inductor 38 with one or more induction coils 8 and encircles preferably the electronic unit 5 in lateral direction. An associated inductor or induction coil overlapping this is disposed at or on the second carrier layer 20 (illustrated by dashed lines, since hidden by the first carrier layer 10), which forms a constituent of the second conductor structure 2 and opens at both of its ends into two elongated conductor track portions 9, which are situated outside the overlap region and likewise belong to the second conductor structure 2. The second conductor structure 2, which is thus coupled or can be coupled inductively to the first conductor structure 1, may in turn form a sensor for detection of any parameter whatsoever, for example of the humidity, or alternatively comprise another sensor, for instance a contact sensor or an antenna. Whereas the second conductor structure 2 in FIG. 4 is constructed as a monopole antenna, it may alternatively also be constructed as a dipole antenna or as any other antenna.

In all figures and embodiments of this Application, the first and/or second conductor structures 1, 2 may be disposed, instead of on the outside 10a, 20a of the respective carrier layer 10, 20, alternatively also on its inside 10b, 20b. Thus, in contrast to the layer structure as illustrated by way of example in FIG. 1, the first conductor structures 1 or the second conductor structures 2 of both of them may be disposed between the mutually facing main surfaces of the two carrier layers 10, 20. However, even then they extend and/or they are isolated from one another by an adhesive or some other intermediate layer in such a way that no current, especially no direct current, is able to flow between them, i.e. both conductor structures are preferably dimensioned and designed as conductor layers isolated galvanically from one another.

Figure 6:
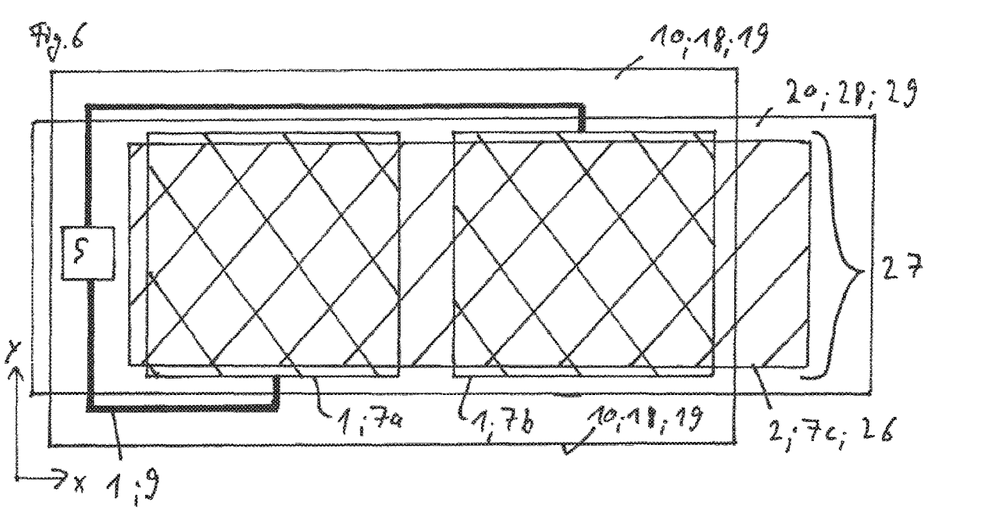
FIG. 6 shows an exemplary embodiment of an object with a capacitive bridge.

FIG. 6 shows a further embodiment, in which two relatively expansive capacitor plates 7a, 7b on the first carrier layer 10 are joined via corresponding conductor tracks 1; 9 to the electronic unit 5. In contrast, on the second carrier layer 20, the second conductor structure 2 forms a third capacitor plate 7c, which acts as a capacitive bridge 26; it bridges the lateral distance between two capacitor plates 7a, 7b of the two first conductor structures 1. FIG. 6 is further an example of an embodiment in which two first conductor tracks 1; 7a, 7b but only one single second conductor track 2; 7c are present. The capacitor 27 formed from the first and second conductor tracks 1, 2 possesses a capacitance that is composed of the partial capacitances of the layer structure in the overlap region, namely on the one hand between the capacitor plates 7a and 7c and on the other hand between the plates 7c and 7b. The electrically isolated capacitor plate 7c possesses approximately double the capacitor surface of each of the other capacitor plates 7a, 7b.

The spacing between the capacitor plates 7a and 7b may be chosen to be large enough to reduce an interfering capacitance between them. Just as in the other figures, the measurements, overlap regions and dimensionings as well as size ratios of the carrier layers 10, 20 or foils 19, 29 or material films 18, 28 are illustrative, i.e. merely exemplary and not to scale.

The object 100 according to FIG. 6, but likewise also of FIGS. 1 to 5, can be formed, for example, as a sensor for measurement of the humidity of the ambient atmosphere or for some other sensor. Preferably, a material, the layer thickness of which is independent of the atmospheric humidity or any other parameters to be detected or to be measured or to be monitored is then used as the intermediate layer 14 between the two carrier layers 10, 20. Alternatively, however, it is also possible to use a material, the layer thickness or its other material property (for instance polarization, dielectric constant, magnetization or the like) varies as a function of the atmospheric humidity or some other measurable parameter. The object of the Application, especially in the embodiment according to FIG. 6, is suitable in particular for measuring sensors with humidity-dependent or parameter-dependent and therefore variable layer thickness of the intermediate layer 14; 13, i.e. for measuring sensors with at least one intermediate layer, the layer thickness of which varies as a function of physical and/or chemical parameters. It is likewise suitable for measuring sensors with at least one intermediate layer, the dielectric constant of which varies as a function of physical and/or chemical parameters.

Figure 7:
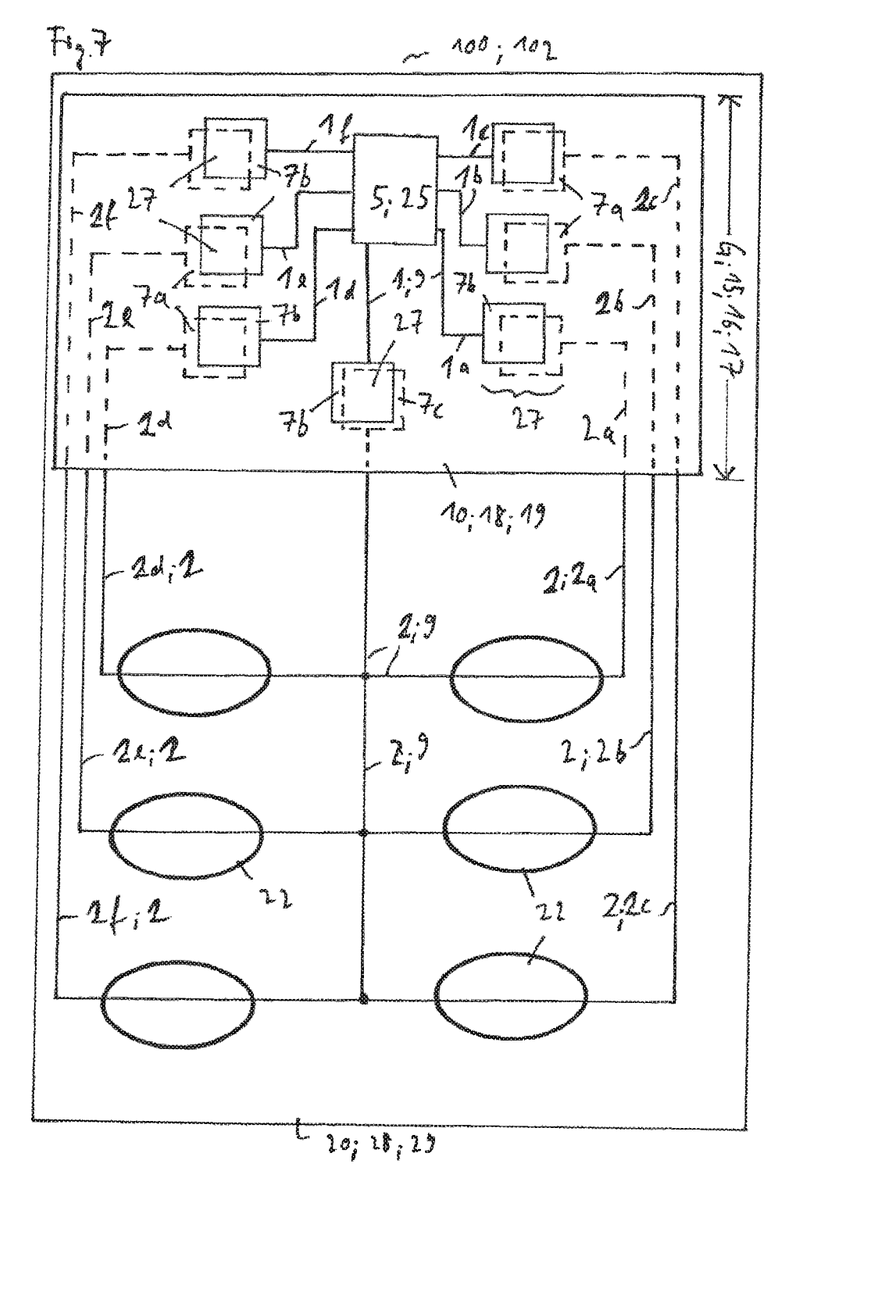
FIG. 7 shows an exemplary embodiment of an object formed as a blister pack.

FIG. 7 shows an alternative embodiment, in which the object 100 is constructed as a blister pack 102 or in any case as a part thereof. The blister pack 102 possesses a plastic foil, which is molded regionally as cavities 22, into which the tablets, capsules or other medicine units are placed, as well as a cover foil for sealing the cavities. According to the invention, the cover foil is formed at least regionally as a double foil, comprising the two carrier layers 10, 20. Thus the object 100 may be a cover foil of a blister pack. The electronic unit 5, which may comprise an RFID chip 25 or any other NFC transponder (if applicable with antenna; not illustrated), is mounted on the first carrier layer 10, which overlaps the surface region of the cavities but does not have to. However, at least the second carrier layer 20 overlaps and seals the cavities 22 filled with tablets or capsules and also extends beyond their surrounding regions. The second conductor structure 2; 9 comprises conductor tracks 2a to 2f, which respectively extend beyond individual cavities 22 and are interrupted, i.e. destroyed, during removal of the respective tablets. For a count of N cavities (N=6 here), therefore N (therefore six here) individual second conductor structures 2 are provided, which are branched by an additional further connecting line 2; 9 which, according to FIG. 7 for example, joins the branch or node points with one another and is coupled galvanically via its own capacitor (with the capacitor plates 7b and 7c) and via a first line 1; 9 to a first terminal of the electronic unit 5 on the first carrier layer 10. The other second conductor tracks 2a to 2f; 9 are respectively connected via further capacitors (with the capacitor plates 7a and 7b) and via further first conductor structures 1a to 1f to further terminals of the electronic unit 5. Thus, for N cavities, in total N+1 first and second conduction branches and therefore also N+1 terminals are necessary on electronic unit 5. With these, the removal of the respective tablet and/or the time of removal can be respectively detected, saved and/or evaluated individually. Otherwise the blister pack of FIG. 7 can be combined with every conventional blister pack; as regards the other individual features, reference is made to the foregoing figures. The second carrier layer 20 overlaps with the first carrier layer 10 at least in a rim region laterally outside the cavities, but is also joined to the more stable foil, which is molded to cavities 22 and for this possesses a higher mechanical strength, stiffness and/or layer thickness than the carrier layers 10, 20.

Figure 8:
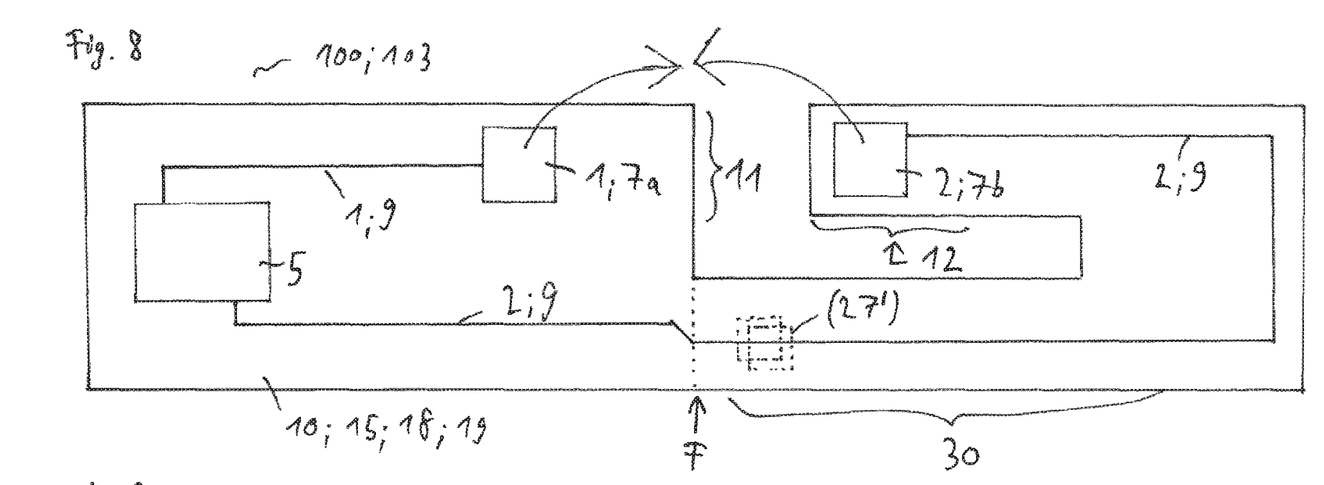
FIG. 8 shows a schematic overhead view of an object formed as an electronic seal.

FIG. 8 shows a schematic overhead view of an object 100 formed as an electronic seal 103. The object 100 has two conductor structures 1, 2 and an electronic unit 5 connected between them. At least one of the two conductor structures 1, 2 comprises a conductor track 9, which extends predominantly outside the electronic unit 5; according to FIG. 8, this is the case for both conductor tracks 1, 2. Each conductor track 1, 2 may additionally further comprise a capacitor electrode or capacitor plate 7a, 7b or alternatively an induction coil or inductor (not illustrated). The two conductor structures 1, 2 are designed such that end pieces or at least partial pieces thereof can be coupled to one another, in order to permit a closed alternating current circuit, at the latest when they are fastened or guided up to one another. The base surface of the carrier structure 15 is configured such that it is able to envelop and electronically secure, i.e. seal, an object 105 to be sealed (FIG. 9) or a part thereof. For this purpose, the electronic seal 103 from FIG. 8 possesses a carrier structure 15 of only one single carrier layer 10 (or alternatively with at least one carrier layer 10), for instance of a foil 19 or of a material film 18. According to FIG. 8, both conductor structures 1, 2 are disposed on this carrier layer 10, either on the same foil surface or on opposite surfaces. The base surface of the carrier layer 10 or carrier structure 15 is chosen such that the carrier layer 10 or carrier structure 15 can be folded, creased, bent or in some other way placed together or closed, such that the two carrier layer regions 11, 12 can be guided up to one another and/or adhered to one another, in order to form a layer composite or layer stack 16. For example, two respective end pieces and/or partial pieces of the two conductor structures 1, 2 can be guided up to one another, in order to form a capacitor or a double inductor, wherein the capacitance or inductance or some other transmission property can be monitored periodically, continuously and/or permanently over a time period by the electronic unit 5, in order to detect a potential seal rupture.

In FIG. 8, both carrier layer regions 11, 12 belong to the same foil 19 or carrier layer 10; they are joined to one another by the joint region 30 and are stacked one on the other during placement together of the carrier structure 15. The electronic unit 5 may be disposed on one of the two carrier layer regions 11, 12 or on the joint region 30. Furthermore, at least one of the conductor structures 1, 2 extends in the joint region 30 or through the joint region 30, for instance between the optional fold or crease line F and the second carrier layer region 12 spaced apart therefrom in FIG. 8.

The two conductor structures 1, 2 may optionally be joined conductively with one another or galvanically isolated from one another. The galvanic isolation may be achieved, for example, by the electronic unit 5 itself, i.e. inside it. Alternatively, one of the conductor structures 1, 2 or both of them may be interrupted locally by a capacitor 27' or a double inductor. The two capacitor plates 7a, 7b or inductors rest on opposite main surfaces of the carrier structure 15 or carrier layer.

Figure 9:
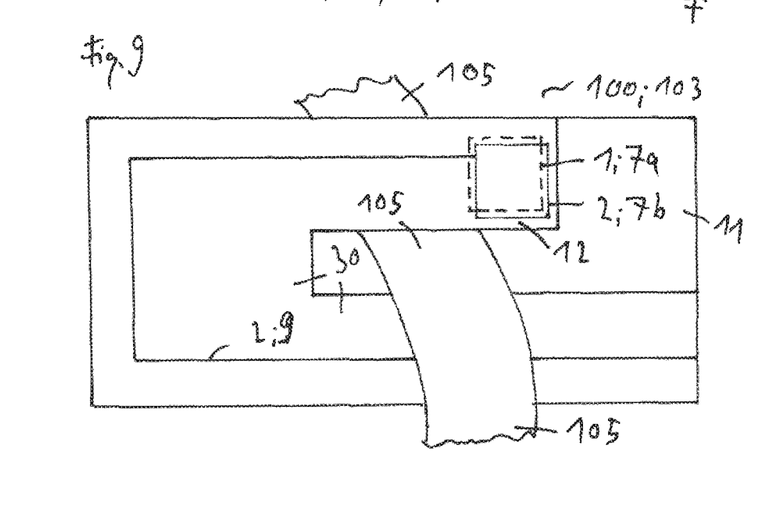
FIG. 9 shows the electronic seal from FIG. 8 in the placed-together condition.

FIG. 9 shows the electronic seal from FIG. 8 in the placed-together and thus sealed condition. In this case the part of the seal 103 situated to the right of the fold line F in FIG. 8 has been turned back and placed on the part of the electronic seal 103 disposed on the left of the fold line F. In the process, an end piece or partial piece of the second carrier layer region 12, especially an end piece of partial piece of the second conductor structure 2 (here comprising at least one capacitor plate 7b or alternatively inductor or induction coil) is made to rest on or over an associated end piece or partial piece of the first carrier layer region 11 or an end or partial piece of the first conductor structure 1 (here comprising a capacitor plate 7a, alternatively inductor or induction coil). By the bending, folding, creasing, placing together or other manner of closing of the carrier structure 15 or carrier layer 10, the electronic seal 103 is closed, wherein an alternating current is also activated, which may also flow through the layer stack between two carrier layer regions 11, 12 (or end or partial pieces of the two conductor structures 1, 2).

Before the closing of the seam 103, an object 105 to be sealed was therefore enveloped (FIG. 9), for example by guidance of the joint region 30 around a part of the object 105. As soon as the alternating current circuit is closed, i.e. the electronic unit 5 and/or the electronic seal 103 is activated, any interruption of the alternating current circuit or change of the capacitance or inductance between the two conductor structures 1, 2 is detected in the layer stack 16 and interpreted as a seal rupture. In addition, the seal rupture may also be indicated by supplementary optical indications (e.g. VOID effect) or by mechanical destruction (e.g. by irreversible adhesion).

Figure 10:
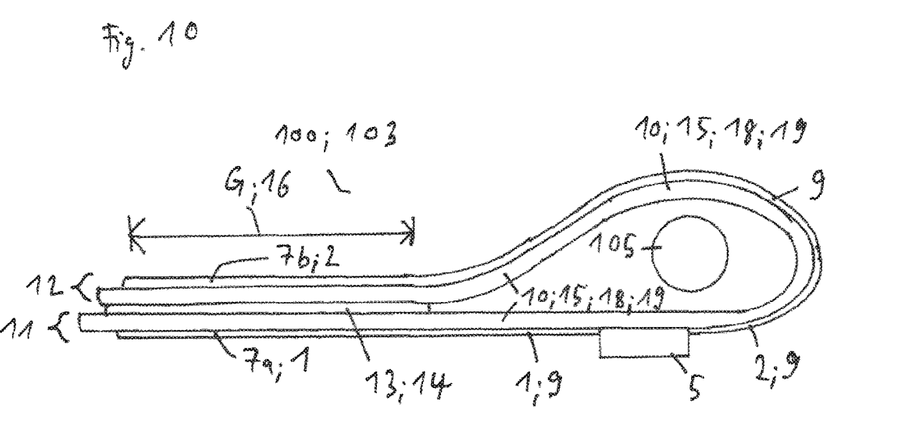
FIG. 10 shows a schematic cross-sectional view of the closed electronic seal from FIG. 9.

FIG. 10 shows a schematic cross-sectional view of the closed electronic seal 103 from FIG. 9. In this case, both carrier layer regions 11, 12 of the carrier structure 15 are stacked one on the other and thus form a layer stack 16.

According to FIGS. 8 to 10, not only the first carrier layer region 11 but also the second carrier layer region 12 is a carrier layer region of the first carrier layer 10. Thus a layer stack 16 can be formed in the region of the base surface region G by means of only one single carrier layer 10, i.e. a single-layer carrier structure 15. Optionally, an adhesive layer 13 or other intermediate layer 14 may be included. The position of the electronic unit 5 in FIGS. 8 to 10 is merely exemplary. Alternatively, it may also be disposed where one of the capacitor plates 7a or 7b is illustrated in FIG. 8. One of the conductor tracks may even be integrated completely into the electronic unit 5 or disposed completely over or under it. Furthermore, the conductor structures 1, 2 or one of them may have vias through the carrier layer 10, for example at the position of the optionally illustrated capacitor 27' in FIG. 8. Thus at least one of the conductor structures may be situated in portions on each of the two main surfaces of the carrier structure 15 or carrier layer 10. The structure, the geometry and the proportions of the objects, which are illustrated in the figures of this Application, are otherwise merely exemplary.

Alternatively, it may also be disposed where one of the capacitor plates 7a or 7b is illustrated in FIG. 8. One of the conductor tracks may even be integrated completely into the electronic unit 5 or disposed completely over or under it. Furthermore, the conductor structures 1, 2 or one of them may have vias through the carrier layer 10, for example at the position of the optionally illustrated capacitor 27' in FIG. 8. Thus at least one of the conductor structures may be situated in portions on each of the two main surfaces of the carrier structure 15 or carrier layer 10. The structure, the geometry and the proportions of the objects, which is illustrated in the figures of this Application, are otherwise merely exemplary.

Whereas, according to FIG. 10, the electronic seal of FIG. 8 is placed together or guided together such that the two conductor structures are situated in the region of the layer stack 16 on surfaces or outsides of the two carrier layer regions 11, 12 facing away from one another, the electronic seal 103 of FIG. 8 (and equally well that of FIGS. 11 and 12, see below) may alternatively also be placed together or guided together such that the two conductor structures in the region of the layer stack 16 are disposed on the surfaces or insides of the two carrier layer regions 11, 12 facing one another.

Furthermore, the electronic seal 103 may also be guided together such that or guided together as a closed strap such that, in the region of the layer stack 16, one of the two conductor structures is disposed on the inside—relative to the arrangement inside the layer stack 16—of the respective carrier layer region, whereas the other conductor structure is disposed on the outside of the (other) carrier layer region; then precisely one of the two conductor structures is facing the adhesive layer. In this embodiment, the carrier layer may be rotated additionally by 180° during guidance together in the transition or joint region between the two carrier layer regions.

Figure 11:
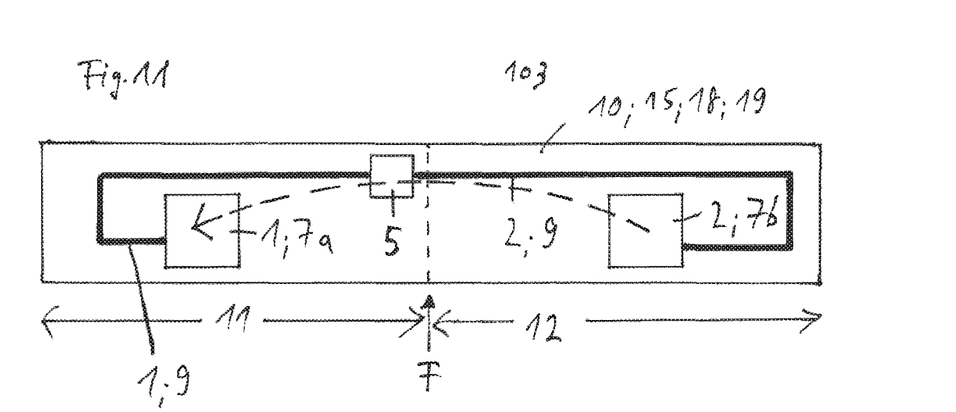
FIG. 11 shows a further embodiment of an electronic seal as an alternative to FIG. 8
Figure 12:
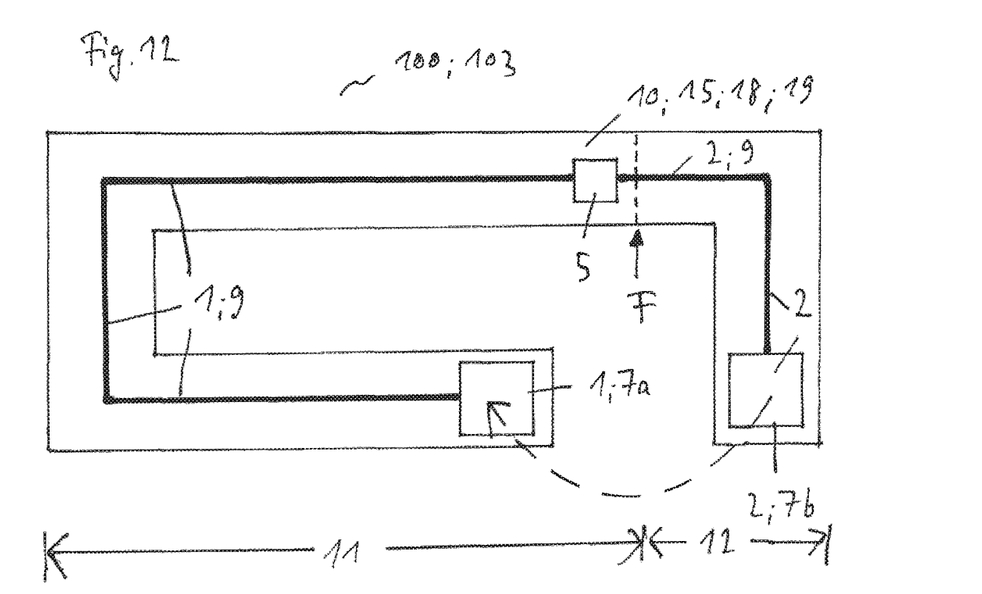
FIG. 12 shows yet a further embodiment of an electronic seal as an alternative to FIGS. 8 and 11.

FIGS. 11 and 12 show embodiments, alternative to FIG. 8, of electronic seals 103 that can be turned back together or folded together, in which especially the surface subdivision of the carrier layer 10 is configured differently. Once again, by the envelopment of an object 105, when it is guided into the vicinity of the crease line F on the carrier layer 10 and enveloped on both sides by the carrier layer regions 11, 12 provided with the conductor structures 1 and 2 or capacitor plates 7a, 7b, a closed alternating circuit around the object 105 is made possible; similarly to that illustrated in FIGS. 9 and 10.

The surface configurations and surface subdivisions shown in FIGS. 8, 11 and 12 are merely exemplary.

REFERENCE SYMBOL LIST 1 first conductor structure
2 second conductor structure
2a-2f antenna
3 sensor element
4 electronic unit
7; 7a, 7b, 7c capacitor plate
8 induction coil
9 conductor track
10 first carrier layer
10a outside
10b inside
11 first carrier layer region
12 second carrier layer region
13 adhesive layer
14 intermediate layer
15 carrier structure
16 layer stack
17 layer composite
18 first material film
19 first foil
20 second carrier layer
20a outside
20b inside
21 second carrier layer region
22 cavity
25 RFID chip
26 capacitive bridge
27; 27' capacitor
28 second material film
29 second foil
30 joint region
38 inductor
100 object
101 moisture sensor
102 blister pack
103 electronic seal
105 sealed object
F fold or crease line
G base surface region
x first lateral direction
z second lateral direction

The invention claimed is:

1. An object (100), which has at least the following:
   at least one first conductor structure (1),
   at least one electronic unit (5),
   at least one second conductor structure (2), which is galvanically isolated from the first conductor structure (1) and/or from the electronic unit (5) but is coupled or can be coupled electrically thereto, and
   a carrier structure (15) with at least one first pliable carrier layer (10), a first carrier layer region (11) of the first pliable carrier layer (10) and with a second carrier layer region (12; 21),
   wherein the carrier structure (15) is opaque and formed as a layer stack (16) in a base surface region (G), which comprises at least one part of the base surface of the carrier structure (15),
   wherein the layer stack (16) in the base surface region (G) comprises at least the first carrier layer region (11) of the first carrier layer (10) and the second carrier layer region (12; 21),
   wherein at least one part of the first (1) and of the second conductor structure (2) is disposed in the base surface region (G),
   wherein the first conductor structure (1) and/or the electronic unit (5) is soldered, bonded to the first carrier layer region (11), adhered or printed on it or joined in some other way with the first carrier layer region (11) and/or worked into it,
   while the second conductor structure (2) is soldered, bonded to the second carrier layer region (12; 21), adhered or printed on it or joined in some other way with the second carrier layer region (12; 21) or worked into it, and
   wherein the second conductor structure (2) is coupled electrically to the first conductor structure (1) in a folded state of the carrier structure by a surface region of the layer stack (16) disposed outside the electronic unit (5).

2. The object according to claim 1, wherein the second pliable carrier layer region (21) comprises a second carrier layer (20) or at least one partial region of another, pliable second carrier layer (20), wherein the first carrier layer region (11) and the second carrier layer region (21) are surface regions of the carrier layers (10; 20), the base surfaces of which overlap one another at least regionally.

3. The object according to claim 2, wherein the first carrier layer (10) and the second carrier layer (20) are adhered to one another, laminated to one another or integrated in some other way into a layer composite (17) at least in the base surface region (G).

4. The object according to claim 2, wherein the layer stack (16) has, between the first carrier layer (10) and the second carrier layer (20), an intermediate layer (14), which permits a capacitive coupling or inductive coupling through the intermediate layer (14).

5. The object according to claim 2, wherein the layer stack (16) has, between the first carrier layer (10) and the second carrier layer (20), at least one adhesive layer (13).

6. The object according to claim 1, wherein the first (10) and/or the second carrier layer (20) is a foil (19; 29).

7. The object according to claim 1, wherein the first (10) and/or the second carrier layer (20) is a material film (18; 28).

8. The object according to claim 1, wherein the first (1) and the second conductor structure (2) are structured conductive coatings, prints of the carrier layer regions (11; 12; 21) and/or of the carrier layers (10; 20) created, for instance with screen printing, flexography or any other printing technique, or conductive structures stamped, adhered onto the carrier layer regions (11; 12; 21) and/or carrier layers (10; 20) and/or created by an etching process or other kind of machining process on the carrier layer regions (11; 12; 21) and/or carrier layers (10; 20).

9. The object according to claim 1, wherein the second conductor structure (2) is an antenna (3) or a sensor element (4), which can be capacitively influenced, of a control panel or of a control element.

10. The object according to claim 1, wherein the second conductor structure (2) comprises a capacitor plate (7), an inductor (28) or induction coil (8) and/or a conductor track (9).

11. The object according to claim 1, wherein the first conductor structure (1) is disposed on the first carrier layer region (11) and/or on the first carrier layer (10) and is galvanically connected to the electronic unit (5) or to individual structural elements or parts of the electronic unit (5).

12. The object according to claim 11, wherein the electronic unit (5) is disposed outside the base surface region (G) of the layer stack (16), in which the first (1) and the second conductor structure (2) are coupled electrically to one another.

13. The object according to claim 11, wherein the first (1) and the second conductor structure (2) together form at least one capacitor (27) or a pair of inductors (28) suitable for inductive transmission in the base surface region (G) of the layer stack (16).

14. The object according to claim 1, wherein the layer stack (16) is a foil composite, layer composite (17) or some other multilayer structure, which permits an electrical measurement, signal transmission and/or the formation, maintenance and/or monitoring of an alternating current circuit.

15. The object according to claim 1, wherein the first (1) and the second conductor structure (2) are disposed on outer surfaces, facing away from one another, of the two carrier layer regions (11; 12; 21) or carrier layers (10; 20) or on their inner surfaces, facing one another, or in that precisely one of the two conductor structures (1, 2) is disposed on that side of the respective carrier layer regions (11; 12; 21) or of the respective carrier layer (10; 20) which is facing the other carrier layer region or regions (12; 21; 11) or the other carrier layer (20; 10).

16. The object according to claim 1, wherein the layer stack (16) is a flat material ply, for example a foil composite or some other layer composite.

17. The object according to claim 1, wherein at least one of the two carrier layer regions is a pliable foil, especially plastic foil or other material ply or a pliable surface portion of a foil.

18. The object according to claim 1, wherein the layer stack (16) is configured such that the spacing, measured in the direction of the layer thickness between two layer regions (11; 12; 21), between two carrier layers (10; 20) and/or between two conductor structures (1; 2), is constant in the base surface region (G).

19. The object according to claim 1, wherein the object (100) is a capacitive moisture sensor (101).

20. The object according to claim 1, wherein the object (100) is a blister pack (102), in which an associated first or second conductor structure (1; 2) is severed at least locally during the removal of a tablet or capsule.

21. The object according to claim 1, wherein the first (1) and/or the second conductor structure (2) comprises a mobile communications antenna or an antenna (3) for NFC signals, Bluetooth, WLAN or other radio systems and/or wherein the electronic unit (5) comprises an RFID transponder or an RFID chip (25).

22. The object according to claim 1, wherein the first conductor structure (1) comprises two capacitor plates (7a, 7b) and wherein the second conductor structure (2) is a capacitive bridge (26) between the two capacitor plates (7a, 7b) of the first conductor structure (1).

23. The object according to claim 1, wherein the second carrier layer region (12) is a further carrier layer region of the first carrier layer (10), which is integrated into the layer stack (16), wherein the first carrier layer (10), at least in places, is bent back, creased, folded and/or formed in some other way to a closed loop, strap or to a ribbon or strip.

24. The object according to claim 23, wherein the object (100) is an electronic seal (103) and wherein the first carrier layer (10) has a joint region (30) extending from the first carrier layer region (11) to the second carrier layer region (12) and wherein at least the electronic unit (5) is interconnected between the first conductor structure (1) and the second conductor structure (2).

25. An object (100), which has at least the following:
at least one first conductor structure (1),
at least one second conductor structure (2),
at least one electronic unit (5), which is interconnected between the first (1) and the second conductor structure (2), and
a carrier structure (15) with at least one pliable carrier layer (10),
wherein the carrier structure (15) is opaque and has at least one first carrier layer region (11), one second carrier layer region (12) and one joint region (30), which joins the first carrier layer region (11) to the second carrier layer region (12),
wherein the carrier structure (15) can be folded, creased, bent back or otherwise placed together, such that
the first carrier layer region (11) and the second carrier layer region (12) are stacked as a layer stack (16), and that,
in a surface region of the layer stack (16) disposed outside the electronic unit (5), which is disposed in the first carrier layer region (11), the first carrier structure (1) in a folded state of the carrier structure is coupled electronically to an end piece or partial piece of the second conductor structure (2), which is disposed in the second carrier layer region (12).

26. The object according to claim 25, wherein the object is an electronic seal (103), the first (11) and second carrier layer region (12) of which be guided up to one another and/or fastened to one another, in order to close an alternating current circuit.

27. A method for manufacturing an object (100), which has an electronic unit and conductor structures on a carrier structure, wherein the method comprises at least the following:
a) application of at least one first conductor structure (1) and at least one electronic unit (5) on a first pliable carrier layer (10) as well as application of at least one second conductor structure (2) on a second pliable carrier layer (20) and
b) finishing of the object (100) by joining, especially adhering or welding, of the first pliable carrier layer (10) with the second pliable carrier layer (20), whereby
a carrier structure (15) is formed which is opaque and, in a base surface region (G) that comprises the at least one partial surface of the base surface of the carrier structure (15), is constructed as a layer stack (16), and whereby
in a surface region of the layer stack (16), which is disposed outside the electronic unit (5), the second conductor structure (2) is coupled electrically to the first conductor structure (1).

\* \* \* \* \*